United States Patent [19]

Rottigni et al.

[11] 4,278,764

[45] Jul. 14, 1981

[54] PROCESS FOR PREPARING CITRIC ACID BY FERMENTATION OF CARBOHYDRATES

[75] Inventors: Claudio Rottigni; Giuliano Cardini, both of Milan, Italy

[73] Assignee: Euteco Impianti S.p.A., Milan, Italy

[21] Appl. No.: 88,303

[22] Filed: Oct. 25, 1979

[30] Foreign Application Priority Data

Oct. 27, 1978 [IT] Italy .................................. 29160 A/78

[51] Int. Cl.³ ............................................... C12P 7/42
[52] U.S. Cl. .................... 435/144; 435/803; 435/813; 435/923
[58] Field of Search .................. 435/144, 803, 813; 562/580

[56] References Cited

U.S. PATENT DOCUMENTS 3,591,455  7/1971  Oppermann ..................... 435/144 X
3,799,840  3/1974  Fukuda et al. ...................... 435/144

Primary Examiner—Lionel M. Shapiro
Attorney, Agent, or Firm—Sughrue, Rothwell, Mion, Zinn and Macpeak

[57] ABSTRACT

The commercial process of preparing citric acid by submerged fermentation of hydrolized carbohydrates under aerobic conditions with yeasts of the genus Candida, while maintaining the pH value at 5-7 by addition of calcium hydroxide, is improved by submitting the broth obtained from a first fermentation operation to a first centrifuging to separate calcium citrate and then to a second centrifuging to separate the yeast cells. The cells thus recovered are recycled for use in a further fermentation operation. The use of said recycle cells permits higher yields and outputs of citric acid to be obtained in the further fermentation operation.

7 Claims, No Drawings

PROCESS FOR PREPARING CITRIC ACID BY FERMENTATION OF CARBOHYDRATES

The present invention relates to a process for preparing citric acid by fermentation of carbohydrates with yeasts as fermentation agents.

Several processes are described in the technical literature for the preparation of citric acid, especially by fermentation of substrates such as linear paraffins and carbohydrates. In particular in the case of linear paraffins there is generally used the submerged fermentation method, with strains belonging to the genus Candida, and in particular to the species *C.fibrae, C.subtropicalis, C.guilliermondii, C.lipolitica, C.oleophila* and *C.zeylanoides*, as described for example in the German Pat. Nos. 2,005,848, 2,050,361, 2,115,514, 2,156,911, 2,212,929 and 2,215,141, U.S. Pat. Nos. 3,689,359 and 3,799,840, British Pat. No. 1,203,006 and French Pat. No. 1,571,551.

For various reasons the current trend is to use carbohydrates (molasses) as substrates, and also in this case the strains commonly used, belonging to the genus Candida, and more particularly to the species *C.Lipolitica* and *C.tropicalis*, as described for example in U.S. Pat. Nos. 2,353,771, 2,394,031, 2,492,673, 3,708,398, 3,708,399, 3,717,549, 2,632,476, 3,741,869, 3,809,612, and 3,083,144. The process basically comprises the following operations of:

- preparing the culture broth in which molasses are diluted with water, reducing the impurity content down to acceptable values and adding measured quantities of nutrient elements;
- sterilizing the apparatus and the fluids;
- introducing the inoculum prepared in a separate culture or taken from a preceding fermentation cycle;
- carrying out the fermentation, which comprises an initial period of multiplication of the inoculated yeast, followed by a period of production of citric acid until the fermentable sugar present in the medium is exhausted.

As is known, the yeasts of the genus Candida require the use of a medium with pH values of from 4 to 7 and the pH is controlled within this range by continuously feeding into said medium a neutralizing agent such as an alkali metal, alkaline earth metal, or ammonium hydroxide. As a result, the citric acid is in salified form in the fermentation medium.

The processes in which citric acid is neutralized in the form of a soluble citrate have drawbacks deriving from the inhibition of the fermentation exerted by the salt, which inhibition increases as the concentration of said salt is increased. In other words there is a limit for the output of citric acid, expressed as the quantity of acid produced per useful volume of the reactor. On the other hand, the precipitation of citric acid in the form of an insoluble salt, with removal of the latter from the fermentation medium, has not been considered until now as a valid solution for the problem under discussion. In fact, a non-negligible fraction of the cells is removed from the fermentation medium, together with the insoluble salt, so that the final balance is unfavourable as regards the conversion products of the sugars, and more particularly as regards the ratio between citric acid and yeast cells produced.

Therefore, an object of the present invention is a process for the preparation of citric acid, deprived or substantially deprived of the above drawbacks. More particularly, according to the present invention, carbohydrates which have been previously hydrolized, are submitted to a submerged fermentation, under aerobic conditions, with a strain of the genus Candida, operating at a controlled temperature, and maintaining the pH at a value of from 5 to 7 by adding calcium hydroxide in measured quantities during the course of the fermentation, this process being characterized in that the fermentation medium is discharged in part during the course of the fermentation, or wholly at the end of the fermentation, and is submitted to centrifuging to separate the calcium citrate from a liquid phase, and the latter is then submitted to centrifuging to separate the yeast cells from the exhausted broth, the cells thus recovered being recycled to the fermentation medium or used for an another fermentation.

Thus, according to the present invention, citric acid is salified, as it forms, with calcium hydroxide, with consequent formation of an insoluble precipitate in the form of granules with a size of the order of 5–50 microns, comprising mainly calcium citrate, in addition to cells. According to the present invention the fermentation broth is first submitted to centrifuging by using a low revolution number to separate the calcium citrate, and the supernatant is submitted to a further centrifuging by using a higher revolution number, thereby to separate the yeast cells from the exhausted broth.

The cells thus recovered, upon possible washing, are recycled or used for another fermentation. It has been ascertained that the centrifuging operations do not lead to a substantial pollution of the treated medium. Moreover, by operating according to the present invention, the quantity of sugar converted into cells is reduced to a minimum, and the overall conversions of sugar into citric acid are higher than those achieved by using the conventional processes. An other advantage consists in the higher output of citric acid, expressed as the quantity of acid produced per useful volume of the reactor. Finally, by operating as described above and under the other conditions which will be specified in the following, there is obtained an acid of high purity, free or substantially free from isocitric acid.

Substrates useful for the fermentation process according to the present invention are molasses, especially of cane or sugar beet, or other similar sugar syrups. These molasses are previously submitted to an "inversion" treatment which consists in the hydrolitic scission of the saccharose present in the same into glucose and fructose, as yeasts of the genus Candida do no allow fermentation of saccharose. The hydrolysis or inversion may be carried out directly on the sugar solution by the chemical or enzymatic method. The chemical hydrolysis is carried out by acidifying the solution, generally with sulphuric acid, heating at elevated temperature and final neutralisation with an inorganic base. The enzymatic hydrolysis is carried out by adding to the sugar solution invertase as an enzyme, operating under weakly acid conditions.

After the hydrolysis treatment, a clarification of the sugar solution is generally carried out, to reduce the content of impurities (especially iron) to values acceptable for the subsequent fermentation.

The fermentation agent useful for the purposes of the present invention is a strain of the genus Candida, especially *Candida lipolitica*, and the fermentation is carried out under submerged conditions, under agitation and in aerobic conditions, with high circulation of oxygen through the reactor. The operating conditions are conveniently as follows:

initial sugar concentration in the culture broth: 200–250 g/l;

neutralizing agent: calcium hydroxide;

fermentation temperature: 28°–32° C., and preferably 29°–30° C.;

pH of the medium: from 5 to 7, values close to neutrality (6–7) being preferred;

feed rate of air: from 0.5 to 1 volume per volume of liquid and per minute.

The apparatus and the fluids (broth and neutralizing agent) are first sterilized and there is then introduced the inoculum deriving from a preceding fermentation cycle or prepared separately, for example by growing the strain for a few days in the same culture broth. During the initial fermentation step, the inoculum greatly multiplies to the expense of the sugar and the other nutrient elements present in the broth, the latter being present in the molasses, or being introduced during the preparation of the sugar solution.

Once the maximum value is reached, the quantity of cells remains practically unchanged, whereas citric acid is produced until the sugar present in the fermentation medium is substantially exhausted. In practice the fermentation operation is stopped when the medium does not require any further addition of neutralizing agent, which indicates the end of the production of the acid. According to an embodiment of the process of the present invention, the medium is submitted at the end of the fermentation to centrifuging at a speed of the order to 500–1500 revolutions per minute for a period of 1–5 minutes to separate the calcium citrate from a liquid phase. Citric acid is then obtained from the calcium citrate by displacement by means of a strong acid according to conventional methods.

The liquid phase is then submitted to centrifuging at a speed of the order of 10,000–20,000 rev. per minute for a period of 1–10 minutes with consequent separation of the yeast cells from the exhausted broth. The cells thus recovered are then used for a further fermentation operation.

According to another embodiment, part of the medium is discharged continuously or intermittengly during the course of the fermentation, and the medium thus discharged is submitted to the two successive centrifugings operating under the conditions described above. The calcium citrate thus separated is submitted to the treatments required for the recovery of citric acid, the cells are recycled to the fermentation medium and the exhausted broth may be recycled upon suitable addition of nutrient substances.

By operating under these conditions, yields in citric acid typically of the order of 60–70% with respect to the sugar fed in are achieved, best results being achieved at about neutral pH values which permit practically theoretical yields in citric acid and yeast cells to be obtained with respect to the converted sugar. The output of citric acid is typically of the order of 130 g/l when using a sugar concentration of 200 g/l.

EXAMPLE 1

(Comparative)

There is used a fermenting apparatus of 14 liter capacity, provided with an agitator with plane blades, a mechanical foam-breaker, a vapor condenser, means for automatically controlling the temperature and pH, and means for measuring the amount of dissolved oxygen.

6.5 liters of an aqueous solution containing about 200 g/l of sugars are loaded into the reacter.

This solution is obtained by dissolving in water cane molasses with a content of saccharose of the order of 50% by weight, submitting to enzymatic hydrolysis said saccharose, and clarifying the solution by treatment with potassium ferrocyanide.

The aqueous sugar solution is admixed with 0.4 g of manganese sulfate monohydrate. The fermenting apparatus is sterilized by heating at 121° C. for 15 min., and then cooled and thermostated at 29° C. There is then added 1 ml of the anti-foaming product commercially known as DB-21 (30% strength) of the Dow Corning Company and 500 ml of the inoculum. The latter is prepared by growing for 2–3 days in a flask, in the same culture broth, a strain of *Candida lipolitica* affording a good production of citric acid.

The reaction mixture ready for fermentation thus contains 1400 g of invert sugar (expressed as saccharose), 10.5 g of yeast cells (as dry matter) and 21 g of citric acid.

Their fermentation is carried out by immission of air (0.5 volumes per volume of liquid and per minute) and by starting the agitator (1400 revolutions per minute). The pH is then controlled to a constant value of 6 by automatical addition of a suspension of calcium hydroxide in water. This last flow is also previously sterilized by heating at 121° C. for 15 minutes. The above operating conditions are maintained until the end of the fermentation, which corresponds to the exhaustion of the fermentable sugar. In particular, the fermentation is stopped at the fifth day, and the concentration of the sugar, the cells and the citric acid in the final broth is determined. The citric acid is mainly present in the form of insoluble calcium citrate, and its concentration is determined, upon acidification of the broth, by the pentabromo-acetone method.

Analysis shows that the broth obtained at the end of the fermentation contains:

cells: 105 g (as dry matter);
titrable-non fermentable-sugar: 133 g;
citric acid: 861 g.

Accordingly, the fermentation yield is 60% based on the sugar fed in. Moreover, the average daily output of the apparatus is 168 g of citric acid.

EXAMPLE 2

The run of Example 1 is faithfully repeated. At the end of the fermentation (5th day), the broth is discharged from the fermenting apparatus and is submitted to centrifuging at 1000 revolutions per minute, for 3 minutes, in a laboratory centrifuge. This treatment permits separation into two phases:

a solid precipitate with a specific weight of about 2, consisting of small granules of calcium citrate, containing also trace amounts of calcium sulfate; this precipitate contains also a very limited number of yeast cells, which, being incorporated into the mass, have not separated;

a supernatant containing soluble compounds (for example primary metabolites) with a specific weight close to 1.

The quantity of citric acid is equal to that obtained in Example 1, that is about 860 g.

The supernatant (about 5 liters of liquid with a cell concentration of 13 g/l) is again submitted to centrifuging at 15,00 revolutions per minute for 5 minutes, thus obtaining the sedimentation of the cells. The cells freed from the exhausted broth are recovered and conveyed to the fermenting apparatus together with 7 liters of a sterilized solution of molasses (clarified and inverted) containing 200 g/l of sugar, and with 1 ml of the aforesaid anti-foaming agent. Thus, the overall composition of the new fermentation broth is as follows:

cells: 65 g
sugar: 1,420 g
citric acid: 20 g

The fermentation is started and carried out under the conditions described in Example 1 for 3 days. At the end of this period of time the broth is submitted to analysis to determine its composition:

cells: 114 g
residual sugar: 140 g
citric acid: 1022 g

On the whole in 8 days of fermentation, there are produced 1842 g of citric acid, with a total yield of 65.7% based on the sugar fed in. Moreover, the average daily output is 230 g of citric acid.

We claim:

1. In a process for preparing citric acid from hydrolized carbohydrates by submerged fermentation under aerobic conditions in a broth containing yeasts of the genus Candida under controlled temperature conditions and at a pH value of from 5 to 7 maintained by adding measured quantities of calcium hydroxide during the fermentation operation, in which the fermentation broth containing citric acid in the form of calcium citrate is discharged during or at the end of the fermentation operation to recover said citric acid, the improvement which comprises subjecting at least part of the fermentation broth thus discharged to centrifuging to separate calcium citrate from a liquid phase containing yeast cells, subjecting said liquid phase to a further centrifuging to separate said cells from a residual broth, and recycling the yeast cells thus recovered for use in a further fermentation operation, thereby achieving by means of the use of said recycle cells an improvement in the yield and output of citric acid in said further fermentation operation.

2. The process of claim 1, wherein said yeasts belong to the species *Candida lipolitica*.

3. The process of claim 1, wherein the fermentation temperature is from 28° to 32° C.

4. The process of claim 1, wherein the fermentation broth has an initial sugar concentration of from 200 to 250 g/l.

5. The process of claim 1, wherein the fermentation is carried out at a temperature of 29°-30° C., at a pH value of 6-7 and with a feed rate of air of from 0.5 to 1.0 volume per volume of broth and per minute.

6. The process of claim 1, wherein the centrifuging of the fermentation broth is carried out for a period of from 1 to 5 minutes at a speed of from 500 to 1,500 r.p.m., and said further centrifuging is carried out for a period of from 1 to 10 minutes at a speed of from 10,000 to 20,000 r.p.m.

7. The process of claim 1, wherein part of the fermentation broth is discharged continuously or intermittently during said fermentation, and the yeast cells recovered are recycled to the fermentation.

* * * * *